DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED SEPTEMBER 21, 1971

890 O.G. 979

T890,001

PROCESS FOR THE QUANTITATIVE DETERMINATION OF THE PRESENCE OF PHENOLICS

Charles Eugene Hamilton, Midland, Mich., assignor to The Dow Chemical Company, Midland, Mich.

Filed Sept. 19, 1969, Ser. No. 859,573
Int. Cl. G01n *33/18*
U.S. Cl. 23—230R
No Drawing. 5 Pages Specification

Method of quantitatively determining the presence of phenolic compounds having an open para-ring position by contacting them with 2,6-dibromoquinone chlorimide at a pH of from 8.5 to 10.5 to form a dibromoindophenol dye. In the known process, the dye is analyzed colorimetrically to determine the concentration of the phenolic in the solution. The improvement comprises contacting the reactants at a temperature within the range from 45° to 50° controlled to ±0.5° C. By carrying out the reaction within this temperature range, the formation of the dibromoindophenol dye takes place in less than 1 hour as compared to a reaction time of as high as 24 hours at room temperature. Reaction times as short as 15 minutes are possible at temperatures within the range of 50±0.1° C.